United States Patent [19]

Oki et al.

[11] Patent Number: 4,870,165

[45] Date of Patent: Sep. 26, 1989

[54] ANTIFUNGAL ANTIBIOTICS

[75] Inventors: Toshikazu Oki, Yokohama; Kyoichiro Saitoh, Zushi; Kozo Tomatsu; Koji Tomita, both of Tokyo; Masataka Konishi, Kawasaki; Takeo Miyaki, Yokohama; Mitsuaki Tsunakawa; Maki Nishio, both of Tokyo, all of Japan

[73] Assignee: Bristol-Myers Company, New York, N.Y.

[21] Appl. No.: 115,273

[22] Filed: Nov. 2, 1987

Related U.S. Application Data

[63] Continuation-in-part of Ser. No. 10,058, Feb. 2, 1987.

[51] Int. Cl.$^4$ .................... A61K 31/70; C07H 15/24; C12P 17/56
[52] U.S. Cl. .................................... 536/6.4; 435/75; 435/170; 536/17.2; 536/18.1; 514/27
[58] Field of Search ..................... 536/6.4, 18.1, 17.2; 514/27

[56] References Cited

PUBLICATIONS

Yasuzawa et al., "The Journal of Antibiotics", vol. XL #8, Aug. '87, pp. 1111–1114 (3–1987).
Matsuda et al., "The Journal of Antibiotics", Aug. 1987, vol. XL #8, pp. 1104–1109.
Konishi et al., #984 Abstract 1987 ICAAC.
Takenghi et al., J. Antibiotics 1988 (Jun.) 41 (6) 807–811.
Gomi et al., J. Antibiotics 1988 (Aug.) 41 (8) 1019–1028.

Primary Examiner—Herbert J. Lilling
Attorney, Agent, or Firm—Mollie M. Yang

[57] ABSTRACT

Novel antibiotic herein designated as BU-3608, BU-3608 B, and BU-3608 C are produced by fermentation of *Actinomadura hibisca* Strain No. P157-2, ATCC 53557, and Strain No. Q278-4, ATCC 53646. The antibiotics possess antifungal and antiviral activities.

6 Claims, 3 Drawing Sheets $^1$H-NMR SPECTRUM FOR BU-3608B
(400 MHz, DMSO-$d_6$)

1H-NMR SPECTRUM FOR BU-3608C
(400 MHz, DMSO-d6)

ANTIFUNGAL ANTIBIOTICS

This application is a continuation-in-part of U.S. Ser. No. 010,058 filed Feb. 2, 1987.

BACKGROUND OF THE INVENTION

The present invention relates to novel antibiotics BU-3608, BU-3608B, and BU-3608C having antifungal and antiviral activities and are useful for treating fungal and viral infections in animals and human beings; to a pharmaceutical composition thereof; to a process for production thereof by fermentation of new microorganisms *Actinomadura hibisca* sp. nov. Strain No. P157-2, ATCC 53557 and Strain No. Q278-4, ATCC 53646; and to the new microorganisms.

SUMMARY OF THE INVENTION

The present invention provides compounds having the formula III

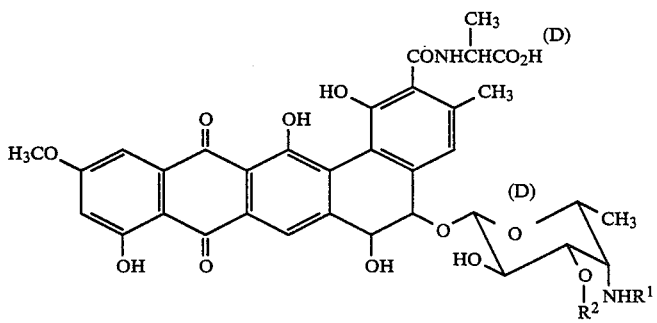

wherein $R^1$ is H and $R^2$ is β-D-xylosyl; or $R^1$ is methyl and $R^2$ is H or β-D-xylosyl; or a pharmaceutically acceptable salt thereof, or an ester thereof.

β-D-xylosyl is the fragment

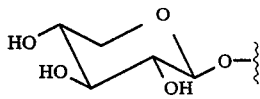

The numbering system for the aglycone portion is given below in Formula IV.

A further aspect of the present invention provides an intermediate having the Formula IV

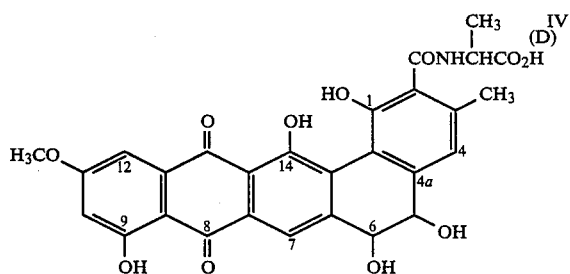

or a salt thereof, or an ester thereof.

Another aspect of the invention provides a process for the production of an antibiotic of formula III by fermentation of an antibiotic-producing strain of *Actinomadura hibisca*.

A further aspect of the invention provides a pharmaceutical composition comprising an antibiotic of formula III and a pharmaceutically acceptable carrier.

Yet a further aspect of the invention provides a method for treating animal and human fungal infections by administering to the afflicted host an effective amount of an antibiotic of Formula III.

Yet a further aspect of the invention provides a method for treating animal and human viral infections by administering to the afflicted host an effective amount of an antibiotic of Formula III.

This invention also provides microorganisms *Actinomadura hibisca* sp nov having the identifying characteristics of Strain No. P157-2 ATCC 53557; and an actinomycete having the characteristics of Strain No. Q278-4, ATCC 53646.

DETAILED DESCRIPTION OF THE INVENTION

ANTIBIOTICS

The antibiotic provided by the present invention and designated BU-3608 is characterized in its free form by the following physico-chemical properties:

Color and form: Red amorphous powder.
Melting Point: 193°–195° C.
Optical rotation: $[\alpha]_D^{26}$ +685° (c 0.1, 0.1N HCl).
Solubility: Soluble in dimethyl sulfoxide, dimethyl formamide, acidic and alkaline water. Slightly soluble in water, methanol, and ethanol. Insoluble in ethyl acetate, chloroform, benzene, n-hexane, and petroleum ether.
IR (KBr): 3340, 3240, 2400, 1720, 1610, 1390, 1295, 1055, 910 cm$^{-1}$.
UV λ max nm (ε): in 50% MeOH: 231 (28,400), 284 (22,700), 481 (9,600); in 0.01N HCl-MeOH: 234 (31,300), 299 (26,700), 459 (11,100); in 0.01N NaOH-MeOH: 240 (33,400), 318 14,700), 499 (15,100).
Elemental analysis: C, 52.99%; H, 5.18%; N, 3.11%.
Secondary ion mass spectrum: m/z 843 (M+3H)$^+$.
Molecular formula: $C_{40}H_{44}N_2O_{18}$.
Thin-layer chromatography: $R_f$ 0.36 (SiO$_2$, MeOAc-n-PrOH-28% NH$_4$OH=45:105:60).

Figure 1:
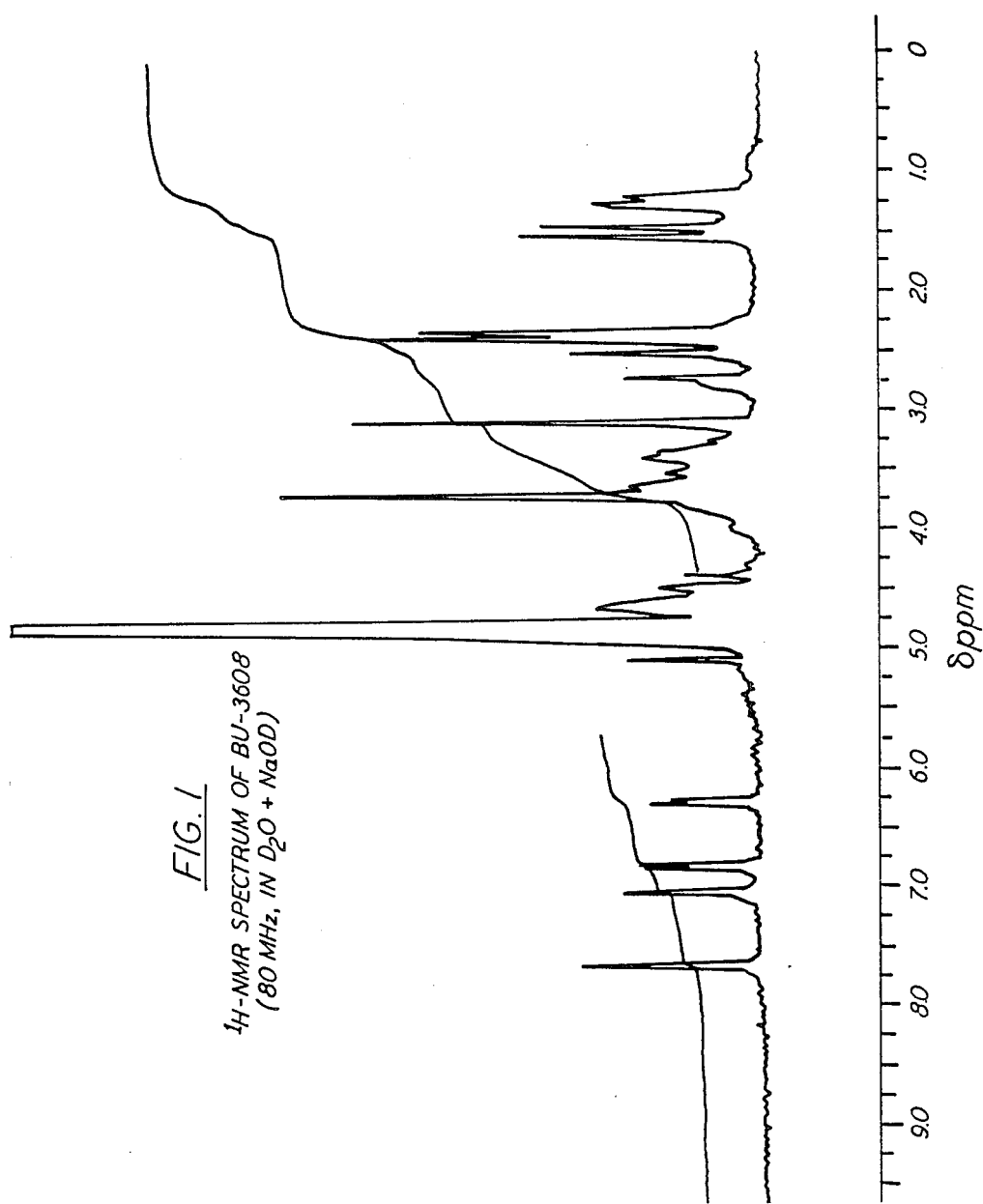
FIG. 1 represents a 80 MHz Proton nuclear magnetic resonance spectrum of BU-3608 in deuterated water and sodium hydroxide-$d_1$ ($D_2O$ + NaOD).

$^1$H NMR (80 MHz, D$_2$O+NaOD): substantially as shown in FIG. 1.

$^{13}$C NMR (100 MHz, DMSO-d$_6$): δppm 187.45(s), 180.55(s), 174.58(s), 168.88:(s), 166.41(s), 166.01(s), 164.12(s), 157.62(s), 143.71(s), 138.04(s), 137.67(s), 136.53(s), 133.10(s), 132.20(s), 126.94(s), 119.29(s), 119.01(s), 116.94(d), 111.60(d), 110.45(s), 106.29(d), 105.29(d), 104.48(d), 104.36(d), 82.68(d), 80.43(d), 76.08(d), 73.77(d), 71.93(d), 70.15(d), 69.57(d), 67.88(d), 65.99(t), 63.37(d), 56.22(q), 48.19(d), 36.63(q), 19.98(q), 17.61(q), 16.36(q).

The structure of BU-3608 has been established based on clear magnetic resonance (NMR) spectroscopy and mass spectrometry (MS) analyses of the antibiotic itself as well as its chemical degradation products. The structure of BU-3608 is given below as formula V. BU-3608 is a unique molecule composed of D-alanine, D-xylose, D-4,6-dideoxy-4-methylaminogalactose, and a polysubstituted dihydrobenz[a]naphthacenequinone chromophore.

Figure 2:
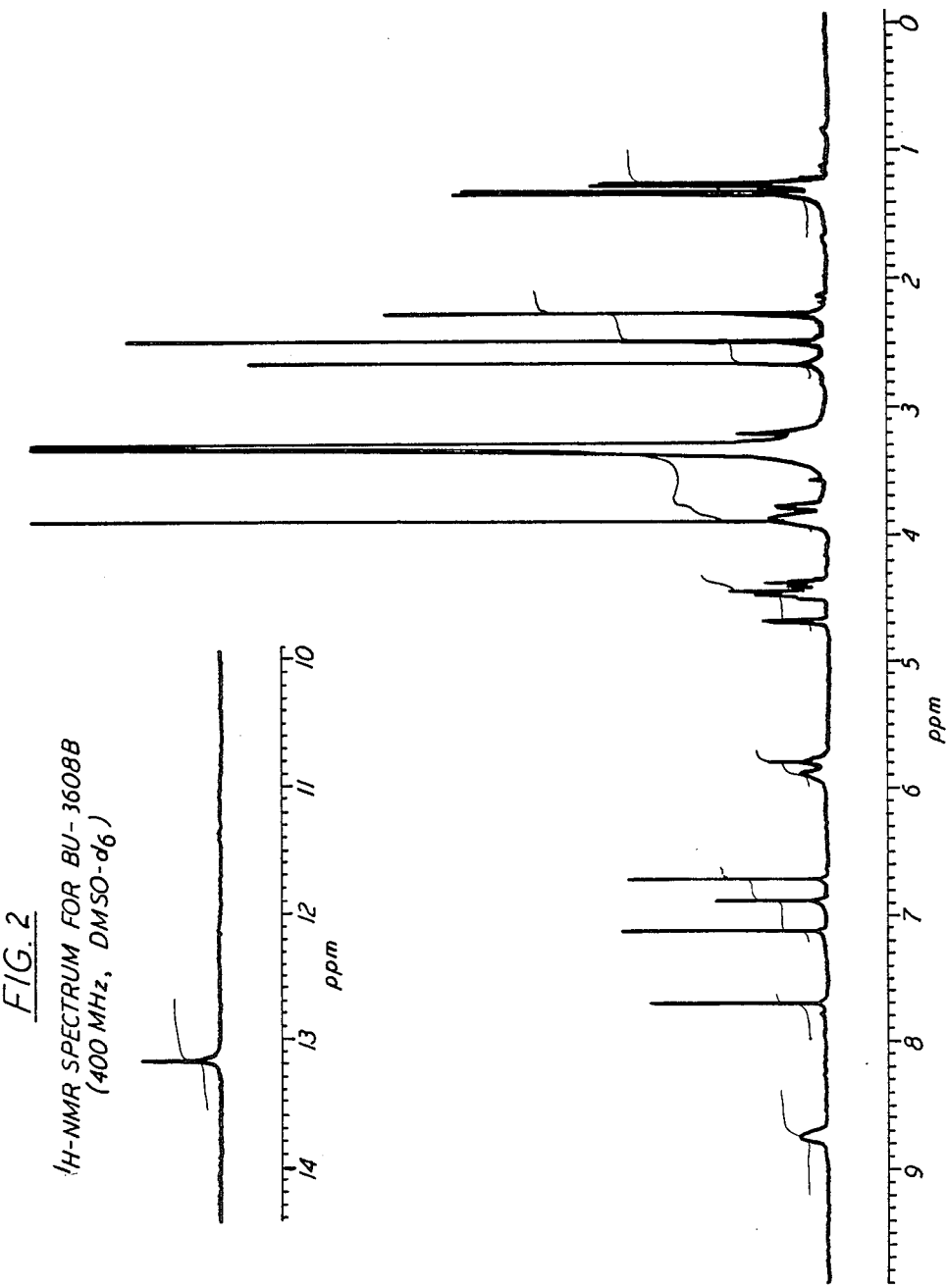
FIG. 2 represents a 400 MHz proton nuclear magnetic resonance spectrum of BU-3608 B in dimethyl sulfoxide-$d_6$.
Figure 3:
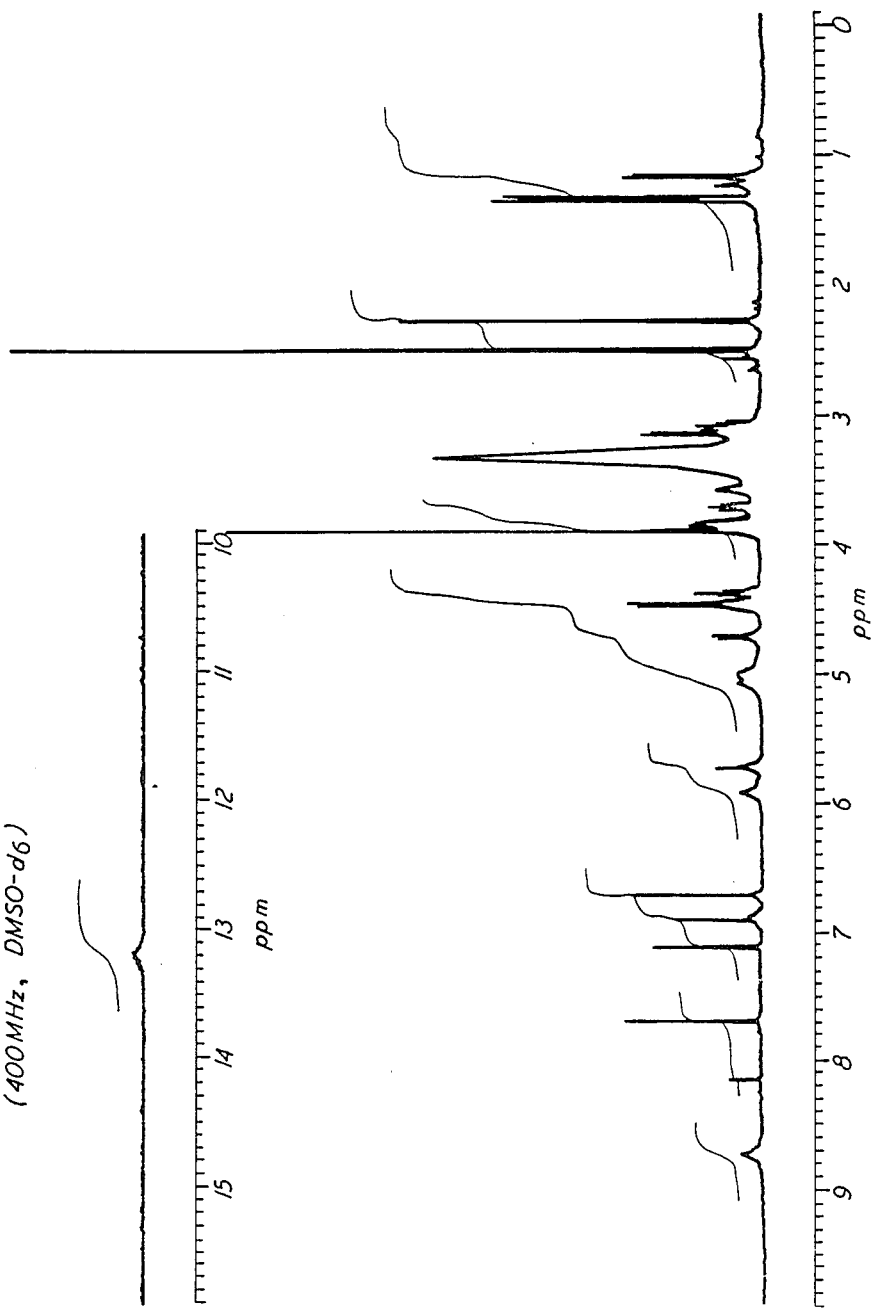
FIG. 3 represents a 400 MHz proton nuclear magnetic resonance spectrum of BU-3608 C in dimethyl sulfoxide-$d_6$.

|  | BU-3608 B | BU-3608 C |
|---|---|---|
| B: in MeOH | 286 (24,100) | 285 (19,700) |
| C: in 50% MeOH | 473 (10,100) | 482 (8,400) |
| B: in 0.01N HCl—MeOH | 234 (31,100) | 233 (31,000) |
| C: in 0.01N HCl-50% MeOH | 296 (27,500) | 297 (26,300) |
|  | 460 (11,100) | 459 (10,900) |
| B: in 0.01N NaOH—MeOH | 241 (33,300) | 241 (30,600) |
| C: in 0.01N NaOH-50% MeOH | 316 (14,200) | 320 (13,800) |
|  | 504 (15,000) | 499 (13,600) |
| IR (KBr) cm$^{-1}$: | 3400, 1600, 1450, 1390, 1295, 1260, 1060 | 3400-3200, 1605, 1390, 1295, 1260, 1140 |
| TLC: | Rf 0.48 | Rf 0.32 |
| (SiO$_2$, MeOAc—n-PrOH—28% NH$_4$OH = 45:105:60 v/v) | | |
| HPLC Rt (min.): | 21.8 | 14.0 |
| (ODS, CH$_3$CN—0.15% KH$_2$PO$_4$ = 7:17, pH 3.5) | | |
| $^1$H NMR: (400 MHz, DMSO-d$_6$) | substantially as shown in FIG. 2 | substantially as shown in FIG. 3 |
| $^{13}$C NMR δ ppm: (100 MHz, DMSO-d$_6$) | 16.3, 17.3, 20.0, 36.8, 47.7, 55.9, 64.0, 67.9, 71.0, 71.2, 71.8, 82.1 | 16.4, 17.5, 19.9, 48.0, 54.3, 56.0, 65.8, 67.6, 69.4, 69.8, 71.9, 73.5, |
|  | 104.0, 104.8, 105.9, 110.2, 111.0, 116.7, 118.8, 119.0, 126.6, 131.9, 133.2, 136.3, 137.6, 137.9, 143.6, 157.3, 163.9, 165.7, 166.7, 168.2, 174.3, 180.2, 187.3 | 76.0, 79.8, 82.5, 104.3, 104.4, 105.1, 106.0, 110.3, 111.2, 116.8, 118.8, 119.0, 126.9, 132.0, 133.0, 136.3, 137.5, 137.8, 143.6, 157.5, 163.9, 165.8, 166.5, 168.2, 174.5, 180.3, 187.2 |

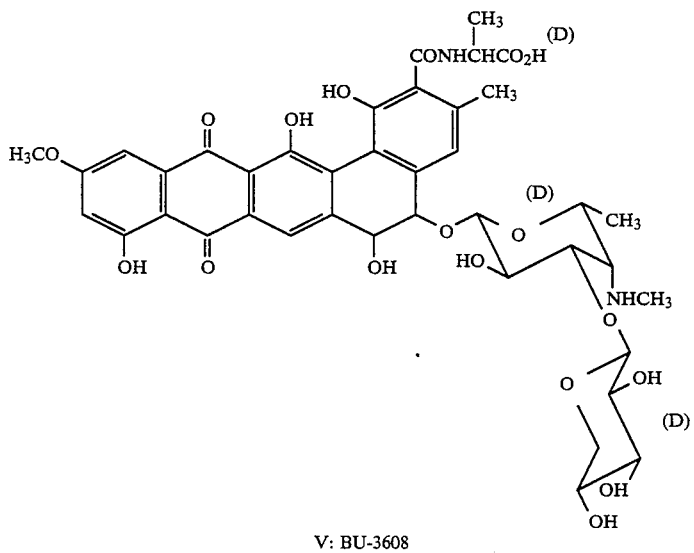

V: BU-3608

Two minor components have also been isolated from the fermentation broth of Strain P157-2. These compounds are designated BU-3608 B and BU-3608 C and are characterized by the physico-chemical properties.

|  | BU-3608 B | BU-3608 C |
|---|---|---|
| Color and form: | dark red powder | dark red powder |
| Melting point (dec.): | 195-198° C. | 220-225° C. |
| Optical rotation: | [α]$_D^{26}$ +440° (C 0.1, 0.1N HCl) | [α]$_D^{24}$ +619° (C 0.1, 0.1N HCl) |
| SIMS m/z: | 711 (M + 3H)$^+$ | 827 (M + H)$^+$ |
| Mol. formula: | C$_{35}$H$_{36}$N$_2$O$_{14}$ | C$_{39}$H$_{42}$N$_2$O$_{18}$ |
| UV λ max (ε): | 234 (30,100) | 230 (24,800) |

The structures of BU-3608 B and BU-3608 C have also been determined and are given as formulas VI and VII, respectively.

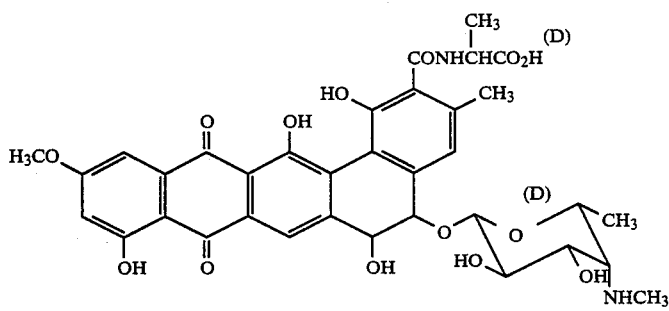

VI: BU-3608 B

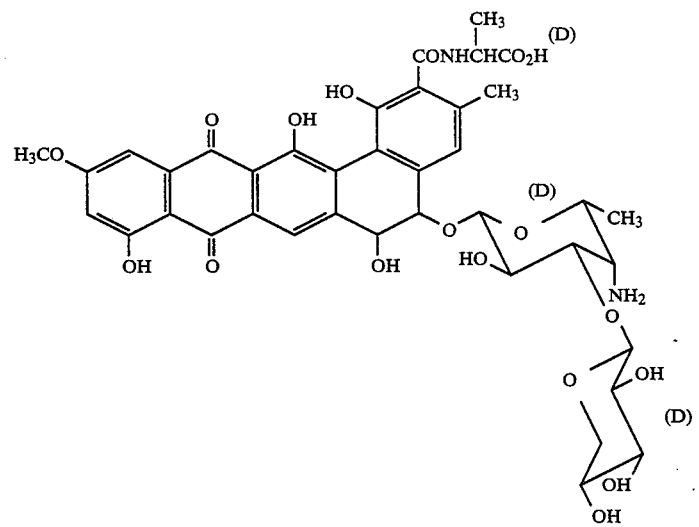

VII: BU-3608 C

Included within the scope of the present invention are the base salts, acid addition salts and internal salts of BU-3608, BU-3608 B, and BU-3608 C. The base salts may be obtained by treating the antibiotics with an organic or inorganic base, for example, sodium hydroxide, calcium hydroxide, ammonium hydroxide, or an amine base such as methylamine, methylethylamine, triethylamine, and pyridine. The acid addition salts may be prepared by addition of a conventionally acceptable acid such as hydrochloric acid, sulfuric acid, phosphoric acid, and the like. A preferred base is sodium hydroxide, and a preferred acid is hydrochloric acid. Also included are physiologically hydrolyzable esters of BU-3608, BU-3608 B, and BU-3608 C which may be prepared using conventional methods well known to those skilled in the art of organic synthesis. The carboxylic acid may react with an alcohol, preferably in the presence of a condensing agent such as dicyclohexylcarbodiimide; or the carboxyl group may be first activated to the corresponding acyl halide, an anhydride, or an active ester or amide. These active acylating agents may then react with the desired alcohol under appropriate reaction conditions to provide the corresponding esters.

The antibiotics of the present invention may be produced by cultivating an antibiotic producing strain of *Actinomadura hibisca* sp. nov. Strain No. P157-2 isolated from a soil sample collected on Fiji Island in the South Pacific. A biologically pure culture of *Actinomadura hibisca* sp. nov. Strain No. P157-2 has been deposited with the American Type Culture Collection, Rockville. Md., and added to their permanent collection of microorganisms as ATCC 53557. Strain P157-2 produces BU-3608 as a major metabolite, and BU-3608 B and BU-3608 C are co-produced as minor components. Subsequent to our previous application, a new actinomycete Strain No. Q278-4 was isolated from a soil sample collected in Andhra Pradesh State, India which produces as major active components antibiotic BU-3608 and BU-3608 C, as well as BU-3608 B as a minor component. Taxonomic study indicates that Strain Q278-4 can be classified as *Actinomadura hibisca*. A biologically pure culture of this microorganism has also been deposited with the ATCC, and assigned the accession number ATCC 53646.

Antibiotic BU-3608 B may also be obtained from BU-3608 Thus acidic methanolysis of BU-3608 yields the methyl ester of BU-3608 B and methyl D-xyloside; the former fragment affords BU-3608 B upon saponification.

BU-3608, BU-3608 B, and BU-3608 C produce the aglycone of formula IV when subjected to acid degradation using concentrated HCl. Compound IV (hereinafter referred to as AG-2) may be used as an intermediate in the synthesis of antibiotics of this invention and derivatives thereof.

The preparation comprises the steps of condensing AG-2, preferably with the non-reacting phenolic hydroxyl groups and the carboxylic acid moiety protected, with a reactive derivative of a protected amino sugar; removing the protecting groups; and isolating the glycoside product having the desired β-linkage. The product having the desired glycosicid linkage may alternatively be isolated prior to the deprotection step.

Protection and deprotection of the functional groups may be effected using standard techniques taught in reference works such as "Protective Groups in Organic Chemistry" by J. F. W. McOmie, Plenum Press, 1973. In general, hydroxyl groups may be conveniently converted into ethers, acetals/ketals, or esters; carboxyl groups are commonly esterified; and amino groups may be converted into amides, ureas, or urethanes. The choice of protecting groups will depend on the exact structures of the starting materials and the final product so that the introduction and removal of the protecting group will not adversely affect the integrity of the rest of the molecule, and also on the reaction conditions the protected compound must tolerate. The protected amino sugar is transformed into a reactive derivative, for example, by treatment with thionyl chloride; the 1-chloro sugar thus formed may be used in situ. The condensation reaction may be effected in inert organic solvent and preferably in the presence of an agent having high affinity for halides, such as silver ion.

Producing Organisms

Characteristics of *Actinomadura hibisca* strain P157-2 and strain Q278-4 are described in detail herein below.

Morphology. Strain P157-2 forms branching hyphae (0.5 to 0.7 μm in width) which develop into substrate and aerial mycelia. Both types of mycelium are long, well-branched, and are not fragmented into rod or coccoid elements. Long (10 to 50 spores per chain) straight chains of spores are formed throughout the aerial mycelium. The spores are oval and cylindrical in shape, 0.4 to 0.6 by 0.7 to 1.2 μm in size, non-motile and have smooth surfaces. Under photomicroscope, a small globose body (2 to 5 μm in diameter) is observed intercalary between or at the tip of the straight spore chains. The globule is determined to be fused coil of the spore chain using scanning electron microscopy. Zigzag hyphae are not observed.

Strain Q278-4 forms branching hyphae which develop into substrate and aerial mycelia. Both types of mycelium are not fragmented into rod or coccoid elements. Long straight chains of spores (10 to 50 spores per chain) are formed in whole parts of the aerial mycelium. The spores are arranged continuously or with intercalation of empty hyphae. A fused coil of spore chain is occasionally observed intercalary between or at tip of long chains, which is seen photomicroscopically as a small globose body (1.5 to 4 μm in diameter). The spores are oval to cylindrical (0.4 to 0.6 by 0.7 to 1.5 μm), non-motile, and have smooth surface.

Cultural Characteristics. The cultural characteristics and carbon source utilization are studied by the methods of Shirling and Gottlieb, Int. J. Syst. Bacteriol., 16:313–340, 1966.

Strain P157-2 grows abundantly on glucose-asparagine agar, moderately in natural organic media such as nutrient agar, Bennett s agar, ISP (International Streptomyces Project Medium Nos. 1, 2, and 6, and poorly in chemically defined media such as sucrose-nitrate agar, ISP Medium Nos. 3, 4, 5, and 7. White aerial mycelium is formed moderately on ISP Medium No. 2, but sparsely on ISP Medium Nos. 3, 4, and 5, and Bennett's agar; pinkish gray aerial mycelium is formed on VDYA agar. Strain P157-2 produces deep red diffusible pigment in many media including ISP Medium Nos. 1, 2, and 6, glucose-asparagine agar, nutrient agar, and Bennett's agar and a brown diffusible pigment in tyrosine agar.

Strain Q278-4 grows poorly in most chemically defined media, and moderately in glucose-asparagine agar and nutritionally rich organic media. The color of aerial mycelium is white but turns to gray on tyrosine agar. Deep red to dark pink, diffusible pigments are produced in all media. In addition, a purplish diffusible pigment is coproduced in Czapek's sucrose-nitrate agar and glucose-asparagine agar, and a brown pigment in tyrosine agar.

The cultural characteristics of Strain P157-2 and Strain Q278-4 are shown in Table 1.

TABLE I

| Cultural Characteristics of Strain P157-2* and Strain Q278-4* | | |
|---|---|---|
| Medium | Strain P157-2 | Strain Q278-4 |
| Sucrose-nitrate agar (Czapek-Dox agar) | ** G: scant<br>A: none<br>S: white to pinkish white (9)***<br>D: pale yellowish pink (31) | poor<br>none<br>colorless to pale purplish pink (252)<br>pale purplish pink (252) |
| Tryptone-yeast extract broth (ISP No. 1) | G: moderate; not turbid<br>A: none<br>S: very deep red (14)<br>D: very deep red (14) | moderate, floccose and not turbid<br>none<br>dark red (16)<br>very deep red (14) |
| Yeast extract-malt extract agar (ISP No. 2) | G: moderate<br>A: moderate; white<br>S: very deep red (14)<br>D: very dark red (17) | good<br>moderate; white<br>deep red (13)<br>very dark red (17) |
| Oatmeal agar (ISP No. 3) | G: poor<br>A: scant; white<br>S: colorless to pale pink (9)<br>D: light pink (4) | poor<br>poor; white<br>colorless to deep red (13)<br>dark pink (6) |
| Inorganic salts-starch agar (ISP No. 4) | G: scant<br>A: scant; white<br>S: colorless to pale pink (9)<br>D: pale yellowish | poor<br>poor; white<br>grayish red (19)<br>colorless |

TABLE I-continued

| Cultural Characteristics of Strain P157-2* and Strain Q278-4* | | |
|---|---|---|
| Medium | Strain P157-2 | Strain Q278-4 |
| | pink (31) | |
| Glycerol-asparagine agar (ISP No. 5) | G: poor | poor |
| | A: scant; white | none |
| | S: colorless to light pink (4) | light grayish red (18) |
| | D: moderate yellowish pink (29) | light yellowish pink (28) |
| Peptone-yeast extract-iron agar (ISP No. 6) | G: moderate | good |
| | A: none | none |
| | S: very dark red (17) | dark red (16) |
| | D: very dark red (17) | very dark red (17) |
| Tyrosine agar (ISP No. 7) | G: poor | poor |
| | A: very scant; white | poor; white, later light gray (264) |
| | S: light brown (57) | dark reddish brown (44) |
| | D: deep brown (59) | dark grayish reddish brown (47) |
| Glucose-asparagine agar | G: abundant | moderate |
| | A: none | none |
| | S: very deep red (14) | dark red (16), later dark grayish purple (229) |
| | D: very dark red (17) | grayish purplish pink (253) |
| Nutrient agar | G: moderate | moderate |
| | A: none | none |
| | S: moderate red (15) | moderate red (15) |
| | D: dark red (16) to blackish red (21) | deep red (13) |
| Bennett's agar | G: moderate | moderate |
| | A: scant; white | poor; white |
| | S: moderate red (15) | deep red (13) |
| | D: very deep red (14) | very dark red (17) |
| VDYA agar | G: moderate | |
| | A: moderate; pinkish gray (10) | |
| | S: very deep red (14) | |
| | D: very dark red (17) | |

*Observation after incubation at 28° C. for 3 weeks.
**Abbreviations:
G = growth;
A = aerial mycelium;
S = substrate mycelium;
D = diffusible pigment.
***Color and number in parenthesis follow the color standard in "Kelly K. L. and D. B. Judd: ISCC-NBS color-name charts illustrated with Centroid Colors. U.S. Dept. of Comm. Cir. 553, Washington, D.C., Nov. 1975".

Physiological Characteristics. The growth of strain P157-2 is inhibited in 5% NaCl but not in 3% NaCl. The growth temperature ranges from 18 to 40° C. Tyrosinase activity is negative. Among 25 carbohydrates, D-ribose, D-glucose, sucrose, cellobiose, trehalose, and salicin are utilized for growth, whereas glycerol, L-arabinose, D-xylose, L-rhamnose, D-galactose, D-fructose, D-mannose, raffinose, and D-sorbitol are not.

The physiological characteristics and carbon source utilization patterns of Strain P157-2 and Strain Q278-4 are listed side-by-side in Tables II and III, respectively. Additional characteristics including the metabolic reactions on nucleic acid bases, organic acids, and carbohydrates have been determined by the methods described in Gordon, R. E. et al, J. Gen. Microb., 109:69–78, 1978; these are shown in Table IV.

TABLE II

| Physiological Characteristics of Strain P157-2 and Strain Q278-4 | | |
|---|---|---|
| | STRAIN Q278-4 | STRAIN P157-2 |
| Hydrolysis of: | | |
| Gelatin | + | + |
| Starch | − | − |
| Milk coagulation | − | − |
| peptonization | + | + |
| Production of: | | |
| Nitrate reductase | +, + | −, +* |
| Tyrosinase | − | − |
| Tolerance to: | | |
| Lysozyme, 0.01% (w/v) | + | + |
| NaCl, 3% (w/v) | + | + |
| 5% (w/v) | +(weak) | − |
| Growth at: | | |
| pH 5.0–12.0 | + | + |
| pH 4.5, 12.5 | − | − |
| Temperature: | | |
| Growth range | 16° C.–43° C. | 18° C.–40° C. |

TABLE II-continued
Physiological Characteristics of Strain P157-2 and Strain Q278-4

|  | STRAIN Q278-4 | STRAIN P157-2 |
|---|---|---|
| No growth | 14° C., 45° C. | 15° C., 43° C. |

*Negative in Czapek's sucrose-nitrate broth, and positive in peptone-nitrate broth.

TABLE III
Carbon Source Utilization of Strain P157-2* and Strain 0278-4*

| Utilization of: | Strain Q278-4 | Strain P157-2 |
|---|---|---|
| Glycerol | − | − |
| D-Arabinose | − | − |
| L-Arabinose | − | − |
| D-Xylose | − | − |
| D-Ribose | + | + |
| L-Rhamnose | − | − |
| D-Glucose | + | + |
| D-Galactose | + | − |
| D-Fructose | + (weak) | − |
| D-Mannose | − | − |
| L-Sorbose | − | − |
| Sucrose | + | + |
| Lactose | − | − |
| Cellobiose | + | + |
| Melibiose | − | − |
| Trehalose | + | + |
| Raffinose | − | − |
| D-Melezitose | + (weak) | − |
| Soluble starch | + | − |
| Cellulose | − | − |
| Dulcitol | − | − |
| Inositol | − | − |
| D-Mannitol | − | + (weak) |
| D-Sorbitol | − | − |
| Salicin | + (weak) | + |

*Observation after incubation at 28° C. for 3 weeks. Basal medium: Pridham-Gottlieb's medium (ISP Medium No. 9) with $CuSO_4.7H_2O$ omitted.
Symbols: + = utilization;
− = no utilization.

TABLE IV
ADDITIONAL PHYSIOLOGICAL CHARACTERISTICS OF STRAIN Q278-4 and STRAIN P157-2

| | STRAIN Q278-4 | STRAIN P157-2 | | STRAIN Q278-4 | STRAIN P157-2 |
|---|---|---|---|---|---|
| Hydrolysis of: | | | Acid from: | | |
| Adenine | + | + | Glycerol | − | − |
| Casein | + | + | D-Arabinose | − | − |
| Esculine | + | + | L-Arabinose | − | − |
| Hippuric acid | − | − | D-Xylose | − | − |
| Hypoxanthine | + | + | L-Rhamnose | − | − |
| Tyrosine | + | + | D-Glucose | + | + |
| Urea | − | − | D-Mannose | − | − |
| Xanthine | − | − | Lactose | − | − |
| | | | Cellobiose | + | + |
| Survival at 50° C., 8 hr | + | + | Melibiose | − | − |
| | | | Trehalose | + | + |
| Utilization of: | | | Raffinose | − | − |
| Benzoate | + | + | D-Melezitose | − | − |
| Citrate | − | − | Inositol | − | − |
| Mucate | − | − | D-Mannitol | − | − |
| Succinate | +(w) | − | D-Sorbitol | − | − |
| Tartrate | − | − | Erythritol | − | − |
| | | | Adonitol | − | − |
| | | | Methyl α-glucoside | − | − |

Chemotaxonomy. Diagnostic amino acid and sugar in whole cell hydrolysate are analyzed by the methods described in Becker B. et al, Appl. Microbiol., 12:421–423, 1964. Phospholipid and mycolate are analyzed by methods described in Lechevalier, M. P. et al, Biochem. Syst. Ecol., 5:249–260, 1977 and in Minnikin D. E. et al, J. Gen. Microbiol., 88:200–204, 1975. Menaquinone is determined by the method of Collins M. D. et al, J. Gen. Microbiol., 100:221–230, 1977. The Presence of meso-diaminopimelic acid, galactose, and a small amount of madurose in the whole cell hydrolysate of strain P157-2 indicates the strain as an actinomycete of cell wall type III and sugar pattern B. The strain has type PI phospholipids and contains MK-9(H6) as the major menaquinone. Glycolate test is negative. Mycolate is absent.

The whole cell hydrolysate of strain Q278-4 contains meso-diaminopimelic acid, glucose, and madurose. This pattern is indicative of type III cell wall and sugar pattern B. The strain has type I phospholipids containing phosphatidylglycerol, and phosphotidylinositol but lacking nitrogenous phospholipids.

The morphology, cultural and physiological characteristics, and cell chemistry of strain P157-2 place it in the genus Actinomadura. Among the previously described species of genus Actinomadura, A. luzonensis, A. kijaniata, A. albolutea, and A. oligospora are similar to strain P157-2 in the formation of long spore chains (10 to 50 spores per chain). However, these four species are different from strain P157-2 in the following characteristics: A. luzonensis forms predominantly short hook spore chains; contains mannose in the whole cell hydrolysate; and utilizes arabinose, glycerol, inositol, mannitol, mannose, rhamnose, and xylose, but not cellobiose. A. kijaniata forms flexuous or spiral spore chains and greenish aerial and substrate mycelia; does not produce a red pigment; and hydrolyzes urea, xanthine, adonitol, arabinose, glycerol, inositol, mannose, rhamnose and xylose. A. albolutea has Type PIV.

The major characteristics of Strain Q278-4 place it in the genus Actinomadura. Strain Q278-4 is most similar to A. hibisca; however, Strain Q278-4 may be differentiated srom Strain P157-2 in producing a purplish pigment in a few media along with reddish pigments in all media. The physiological characteristics of the two strains also differ as shown in Tables II to IV; however, the differences are not considered enough for separate species. Thus, Strain Q278-4 can be classified as a new strain of A. hibisca.

It is to be understood that the present invention is not limited to use of the particular Strain P157-2 or Q278-4 or to organisms fully answering the above description. It is especially intended to include other BU-3608 producing strains or mutants or variants of said organisms which can be produced from the described organisms by known means such as X-ray radiation, ultraviolet radiation, treatment with nitrogen mustard, phage exposure, and the like.

Antibiotic Production

The antibiotics of the present invention are produced by cultivating *Actinomadura hibisca* Strain No. P157-2 or Strain Q278-4, or a mutant or a variant thereof, in a conventional aqueous medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention. phospholipid; does not produce a red pigment; utilizes arabinose, mannitol, rhamnose and xylose; and does not reduce nitrate to nitrite. *A. oligospora* contains mannose in the whole cell hydrolysate; does not produce a red pigment; decomposes urea but not adenine, hypoxanthine or tyrosine; and does not reduce nitrate to nitrite.

*A. pelletieri* and *A. macra* are related to strain P157-2 from a numerical taxonomy viewpoint. They are differentiated from strain P157-2 by the following characteristics: almost all strains of *A. pelletieri* are asporogenic. If a spore was formed, only short spore chain is observed on rudimentary aerial mycelium. *A. pelletieri* does not hydrolyze adenine, esculin or cellobiose, and is sensitive to lysozyme. *A. macra* forms short spore chain and sparse aerial mycelium; produces a black pigment in ISP Medium Nos. 2 and 3; does not produce a red pigment in any media; and lacks the ability to hydrolyze casein, esculin and cellobiose.

Strain P157-2 produces red benzonaphthacene pigments with antifungal and antiviral activities in both natural organic media and chemically defined media. This class of pigment is unrelated to the previously described red pigments of Actinomadura species, including prodigiosins and anthracyclines.

Thus, Strain P157-2 is considered to be a heretofore undescribed species of the genus Actinomadura, for which the name *A. hibisca* sp. nov. is proposed. The type strain is No. P157-2.

The nutrient medium should contain an appropriate assimilable carbon source such as ribose, glucose, sucrose, cellobiose. As nitrogen source, ammonium chloride, ammonium sulfate, urea, ammonium nitrate, sodium nitrate, etc. may be used either alone or in combination with organic nitrogen sources such as peptone, fish meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron, and the like.

It has been noted that the composition of the nutrient medium for Strain Q278-4 may be chosen to favor the production of either BU-3608 C or BU-3608. For example, addition of an appropriate amount of ammonium sulfate to a BU-3608 producing medium increases the level of BU-3608 C, relative to the level of BU-3608.

Production of antibiotics BU-3608, BU-3608 B, and BU-3608 C may be effected at any temperature conducive to satisfactory growth of the producing organism, e.g. 25°–40° C. and is most conveniently carried out at a temperature of around 27°–32° C. Ordinarily, optimum antibiotic production is obtained in shake flasks after incubation periods of 5–8 days. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture or a lyophilized culture of the organism. After obtaining an active inoculum in this manner, it is aseptically transferred to the fermentation tank medium. Antibiotic production in tank fermentors usually reaches the optimum after 3–6 days of incubation. Agitation in the tank fermentor is provided by stirring and aeration may be achieved by injection of air or oxygen into the agitated mixture. Antibiotic production may be monitored using chromatographic or spectroscopic techniques, or by a conventional biological assay.

ISOLATION AND PURIFICATION OF ANTIBIOTICS

The antibiotics of the present invention may be recovered from the cultivated broth by any suitable method for such recovery. A general scheme for one such method for the isolation and purification of antibiotic BU-3608 from the fermentation broth of Strain P157-2 is shown below as Scheme I.

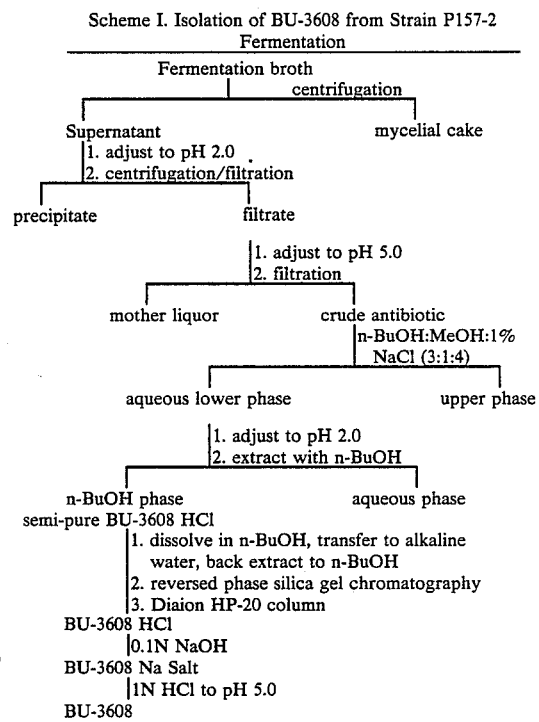

To elaborate on the flow chart of Scheme I, whole fermentation broth is separated into mycelial cake and supernatant by a conventional method such as centrifugation. The supernatant is acidified and the precipitate thus formed is removed. The filtrate is adjusted to pH 5 to deposit crude antibiotic which is collected and partitioned between an water immiscible organic solvent and an aqueous phase; an example of such a solvent system is n-butanol-methanol-1% NaCl mixture. The aqueous phase is separated, acidified, and extracted with an organic solvent such as n-butanol. The extract is concentrated in vacuo and lyophilized to yield semi-pure hydrochloride of BU-3608. A solution of the semi-pure material in n-butanol is shaken with alkaline water to transfer the antibiotic to the aqueous phase which is acidified then extracted with an organic solvent such as n-butanol. Evaporation of the n-butanol extract gives purer sample of BU-3608 HCl, a sample of which is dissolved in water and subjected to revereed phase silica gel chromatography. The active fractions are pooled and evaporated to give an aqueous concentrate which is further purified on an adsorption column such as Diaion HP-20 (supplied by Mitsubishi Kasei). The active fractions are concentrated and lyophilized to give substantially pure BU-3608 HCl. The sodium salt is obtained when BU-3608 HCl is treated with 0.1N NaOH. An aqueous solution of the Na salt when adjusted to pH 5.0 deposits the free form of BU-3608.

Scheme II illustrates the isolation of BU-3608 B and BU-3608 C from above-described semi-pure BU-3608 HCl solids. An aqueous solution of the semi-pure material is subjected to reversed phase silica gel chromatography. The fractions eluting before and after the homogeneous BU-3608 fraction are collected and desalted to afford a BU-3608 C rich fraction and a BU-3608 B rich fraction, respectively. Each of these fractions is chromatographed and again desalted to separate BU-3608 and to provide substantially pure BU-3608 B and BU-3608 C.

Scheme II. Isolation of BU-3608 B and C from Strain No. P157-2

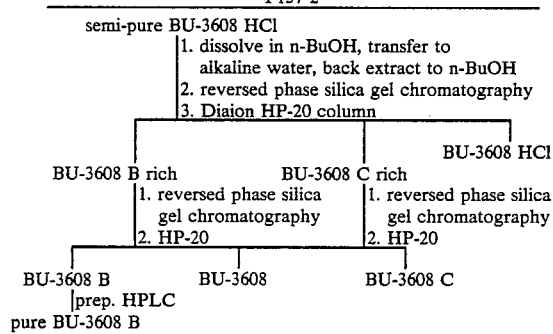

Scheme III exemplifies one procedure suitable for isolating BU-3608 C from the fermentation broth of Strain Q278-4. Whole fermentation broth is centrifuged to remove insoluble materials. The supernatant is acidified and the precipitate formed discarded. The filtrate is adjusted to pH 5.0, and the precipitate collected and partitioned between an aqueous phase and a water-immiscible organic phase. The organic phase is separated and treated with alkaline water. The aqueous layer, after acidification, is chromatographed on a Diaion HP-20 column to afford crude BU-3608 C containing solids. Reversed phase silica gel chromatography of the complex material followed by further purification on Diaion HP-20 column yields pure BU 3608 C.

Scheme III. Isolation of BU-3608 C from Strain Q278-4 Fermentation

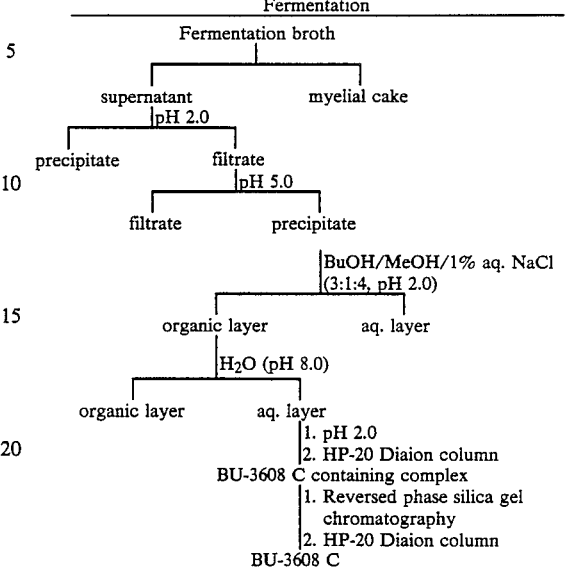

Biological Properties

The antifungal activities of BU-3608, BU-3608 B, and BU-3608 C were evaluated both in vitro and in vivo. The minimum inhibitory concentrations (MICs) against various fungi were determined by serial agar and broth dilution methods using Sabouraud dextrose agar and broth. The inoculum size of the test organism was adjusted to $10^5$ CFUs/ml (BU-3608) or $10^5$–$10^9$ CFUs/ml (BU-3608 B and C) in the agar dilution method, and $10^4$–$10^5$ CFUs/ml (BU-3608) or $10^4$–$10^6$ CFUs/ml (BU-3608 B and C) in the broth dilution method. The MIC values recorded after the cultures had been incubated for 48 or 72 hours are set forth below in Tables V and VI.

TABLE V

IN VITRO ANTIFUNGAL ACTIVITY OF BU-3608 IN SABOURAUD DEXTROSE AGAR AND BROTH

| Test Organism[2] | MIC ($\mu$g/ml[1]) | |
|---|---|---|
| | Agar | Broth |
| Candida albicans IAM4888 | 25 | — |
| Candida albicans A9540 | 25 | 6.3 |
| Aspergillus fumigatus IAM2530 | 3.1 | — |
| Aspergillus fumigatus IAM2034 | 3.1 | 12.5 |
| Trichophyton D155 mentagrophytes | >100 | — |
| Trichophyton #4329 mentagrophytes | 25 | 25 (6.3)[3] |
| Cryptococcus D49 neoformans | 0.8 | — |
| Cryptococcus IAM4514 neoformans | 0.8 | 0.4 |
| Aspergillus flavus FA21436 | 1.6 | — |
| Piricularia oryzae D91 | 3.1 | — |
| Blastomyces dermatitidis D40 | 6.3 | — |
| Sporothrix schenckii IFO8158 | 0.8 | — |
| Petriellidium boydii IFO8073 | 100 | — |
| Mucor spinosus IFO5317 | 50 | — |
| Fusarium moniliforme A2284 | 3.1 | — |

[1]Determined after incubation for 72 hours at 28° C.
[2]Inoculum size: $10^5$ CFU/ml for agar dilution and $10^4$–$10^5$ CFU/ml for broth dilution.
[3]Values in parenthesis indicate partial inhibition.

TABLE VI

BU-3608 B and C in vitro antifungal activity in Sabouraud dextrose agar and broth.

| | MIC (μg/ml)* | | | |
|---|---|---|---|---|
| | BU-3608B | | BU-3608C | |
| Test Organisms** | AGAR | BROTH | AGAR | BROTH |
| Candida albicans IAM4888 | 1.6 | — | 6.3 | — |
| Candida albicans A9540 | 3.1 | 3.1 (3.1) | 6.3 | 6.3 (3.1) |
| Cryptococcus neoformans D49 | 0.8 | — | 0.8 | — |
| Cryptococcus neoformans IAM4514 | 0.8 | 1.6 | 0.8 | — |
| Aspergillus fumigatus IAM2530 | 6.3 | — | 3.1 | — |
| Aspergillus fumigatus IAM2034 | 6.3 | 50 (12.5) | 6.3 | 6.3 (3.1) |
| Fusarium moniliforme A2284 | >100 | — | 6.3 | — |
| Piricularia oryzae D91 | 6.3 | — | 3.1 | — |
| Trichophyton mentagrophytes D155 | 6.3 | — | 3.1 | — |
| Trichophyton mentagrophytes #4329 | 6.3 | 6.3 (3.1) | 6.3 | 6.3 (3.1) |
| Sporothrix schenckii IFO8158 | 3.1 | — | 1.6 | — |

*Determined after incubation for 48–72 hours at 28° C.
**Inoculum size: $10^4$–$10^6$ CFU/ml for broth dilution and $10^5$–$10^9$ CFU/ml for agar dilution.
Values in parenthesis indicate partial inhibition.

In vivo activities of BU-3608, BU-3608 B, and BU-3608 C were tested against *Candida albicans*, *Aspergillus fumieatus*, and *Cryptococcus neoformans* infections in mice. Test organisms were cultured for 18 hours at 28° C. in YGP medium yeast extract, lucose, peptone $K_2HPO_4$, $MgSO_4$) and then suspended in saline. Male ICR mice weighing 20 to 24 g were infected intravenously with about 20 times (BU-3608) or 10 times (BU-3608 B and C) the median lethal dose of the test fungi. The antibiotics at various dose levels were administered to groups of 5 mice each either intravenously just after the fungal infection or intramuscularly twice a day on days 0 and 1. The dose that protects 50% of the animals from infection $PD_{50}$, mg/kg) was calculated from survival rates recorded on the 20th day after the fungal challenge. All control animals died within 7 to 15 days after infection. Results of the in vivo studies are shown in Table VII.

The methyl and ethyl esters of BU-3608 were also evaluated against *C. albicans* A9540 infections in mice using the protocol described above. Antibiotics were given b.i.d. on days 0 and 1 and the $PD_{50}$ values recorded on day 20 are 32 mg/kg/inj. for BU-3608 methyl ester and 16 mg/kg/inj. for BU-3608 ethyl ester. It is postulated that these esters are hydrolyzed in vivo to provide the active parent compound.

TABLE VII

In Vivo Antifungal Activity Against *C. Albicans*, *A. Fumigatus* and *C. Neoformans* Intravenous Infections In Mice

| | | Number of survivors/tested | | | |
|---|---|---|---|---|---|
| | | *C. albicans* A9540 | | *A. fumigatus* IAM 2034 | *C. neoformans* IAM 4514 |
| Compound | Dose | iv* | im** | im** | im** |
| BU-3608 | 50 | 5/5 | 5/5 | | |
| | 25 | 5/5 | 4/5 | 4/5 | 5/5 |
| | 12.5 | 5/5 | 3/5 | 3/5 | 5/5 |
| | 6.3 | 2/5 | 0/5 | 3/5 | 5/5 |
| | 3.1 | 2/5 | 1/5 | 0/5 | 2/5 |
| | 1.6 | 1/5 | | 0/5 | 1/5 |
| $PD_{50}$ (mg/kg/inj) | | 7.2 | 11 | 5.7 | 3.5 |
| BU-3608B | 50 | 4/5 | | | |
| | 25 | 3/5 | 3/5 | | 5/5 |
| | 12.5 | 3/5 | 0/5 | | 3/5 |
| | 6.3 | | 1/5 | | 0/5 |
| | 3.1 | 0/5 | 0/5 | | 1/5 |
| $PD_{50}$ (mg/k/inj.): | | 11 | 22 | | 11 |
| BU-3608C | 55 | | 5/5 | | |
| | 28 | | 5/5 | | |
| | 14 | | 2/5 | | |
| | 6.9 | | 0/5 | | |
| $PD_{50}$ (mg/kg/inj.): | | | 16 | | |

Dose in mg/kg/inj.
*Compounds were administered iv just after fungal challenge.
**Compounds were administered im b.i.d. on days 0 and 1.

The cytopathic effect (CPE) reduction assay was used to evaluate the in vitro antiviral activities of BU-3608 against herpes simplex virus type I (HSV-I) in Vero cells, and influenza virus A in Madin Darby canine kidney (MDCK) cells. A 200 μl aliquot of cell suspension containing $2 \times 10^4$ cells was placed in each well of the microplate. After incubation at 37° C. for 48–72 hours under humidified 5% $CO_2$-95% air atmosphere, the growth medium was drained from the wells and replaced with fresh medium containing the test compound at various doses. For wells designated as virus control, the test compound was omitted from the medium. To each well, except those used for cytotoxicity study, was added 50 μl of growth medium containing the test viruses at a multiplicity of approximately 10 $TCID_{50}$ (50% tissue culture infective dose). The microplate was incubated for a further 72 hours, after which the degree of inhibition of viral-induced CPE and drug-induced cytotoxicity was determined under a microscope. CPE reduction was expressed as $ID_{50}$ (50% inhibitory dose) which is defined as the concentration of compound required to reduce CPE by 50% as compared to the control. virus-infected but untreated cell cultures; cytotoxicity is expressed as $TD_{50}$, the concentration which showed 50% cytotoxicity against Vero or MDCK cells not infected with the viruses. BU-3608 B was similarly evaluated in the influenza A virus-MDCK cell system.

The $ID_{50}$ values for BU-3608 and BU-3608 B against influenza virus A were 4.4 μg/ml and 8.4 μg/ml, respectively. The $TD_{50}$ was over 100 μg/ml for both Vero and MDCK cell lines.

The acute toxicity of BU-3608 was determined in mice after single intravenous and intramuscular administrations. $LD_{50}$ after iv administration was 140 mg/kg; no sign of toxicity was observed after im dose of 400 mg/kg.

For treatment of fungal and viral infections in animals and human beings, the antibiotics of the present invention may be given in an antifungally or an antivirally effective amount by any accepted routes of administration; these include, but are not limited to, intravenous, intramuscular, oral, intranasal, and for superficial infections, topical administration. Preparations for parenteral administration include sterile aqueous or non-aqueous solutions, suspensions or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that when treating a host infected with a virus or fungus susceptible to the antibiotics of this invention, the actual preferred route of administration and dosage used will be at the discretion of the attending clinician skilled in the treatment of fungal or viral infections, and will vary according to the causative organism, its sensitivity to the antibiotic, severity and site of the infection, and patient characteristics such as age, body weight, rate of excretion, concurrent medications, and general physical condition.

The following examples are illustrative without limit the scope of the present invention.

EXAMPLE 1

Fermentation of BU-3608

(a) Agar slant. *Actinomadura hibisca* strain P157-2 was grown on a agar slant consisting of
0.5% soluble starch (Nichiden Kagaku Co.)
0.5% glucose
0.1% fish meat extract (Mikuri Kagaku)
0.1% yeast extract (Oriental Yeast Co.)
0.2% NZ case (Sheffield)
0.1% $CaCO_3$
0.2% NaCl
1.6% agar
The culture was incubated at 28° C. for 7 days.

(b) Seed culture. A portion of the microbial growth from the slant culture was transferred to a 500 ml Erlenmeyer flask containing 100 ml of vegetative medium of the following composition:
1.0% glucose
2.0% soluble starch (Nichiden Kagaku Co.)
0.5% NZ amine A (Sheffield)
0.5% yeast extract (Oriental Yeast Co.)
0.1% $CaCO_3$
The PH of the medium was adjusted to 7.2 before sterilization. The seed culture was incubated at 28° C. for 4 days on a rotary shaker set at 200 rev. per minute.

(c) Flask fermentation. 5 ml of the microbial growth was transferred from the seed culture to a 500 ml Erlenmeyer flask containing 100 ml of sterile production medium of the following composition:
3.0% glucose
3.0% soybean meal (Nikko Seiyu Co.)
0.5% Pharmamedia (Traders Protein)
0.1% yeast extract (Oriental Yeast Co.)
0.3% $CaCO_3$
The fermentation was carried out at 28° C. for 5 to 6 days on a rotary shaker. Antibiotic production in the fermentation broth was monitored by broth dilution method using *Candida albicans* A9540 as the indicator organism in Sabouraud dextrose broth; UV assay at 500 nm in 0.01N NaOH-MeOH (1:1) solution was also used. Antibiotic production reached a maximum at 650 $\mu$g/ml on day 5.

(d) Tank fermentation. 3 l of the seed culture was used to inoculate 120 l of sterile production medium contained in a 200 l tank fermentor. The composition of the production medium is the same as that used in flask fermentation. The tank was operated at 28° C with the agitation rate set at 250 rev. per minute and the aeration rate at 120 l per minute. After 96 hrs of fermentation, an antibiotic potency of 500 $\mu$g/ml was obtained, and the pH of the broth was 7.9.

EXAMPLE 2

Isolation and purification of BU-3608

210 l of harvested broth (pH 7.8) was centrifuged and the supernatural was acidified to pH 2.0 with 6N HCl to deposit bio-inactive solid. After the precipitate was removed, the filtrate was adjusted to pH 5.0 with 6N NaOH and the solution was stirred gently for 30 minutes at room temperature. The resultant dark red solid was filtered off and dried in vacuo.

570 g of the solid (purity: 13%) was dissolved in 160 l of n-butanol-methanol-1% NaCl (3:1:4) mixture and the mixture was stirred for 30 minutes. The lower aqueous layer was separated, washed again with 80 l of fresh upper layer, acidified to pH 2.0 with 6N HCl, and then extracted with 100 l of n-butanol. The n-butanol extract was washed with 20 l of water, concentrated in vacuo and lyophilized to yield 100 g of semi-Pure BU-3608 hydrochloride (purity: 64%). A solution of the solid in 100 l of n-butanol was shaken with 100 l of alkaline water (pH 9.0). The aqueous layer was acidified to pH 2.0 and washed with 100 l of ethyl acetate. Extraction with 95 l of n-butanol followed by evaporation of the solvent gave 52.1 g of purer BU-3608 HCl (purity: 82%).

2.0 g of the antibiotic was subjected to reversed phase silica gel chromatography (ODS-60, 350/250 mesh, Yamamura Chemical Lab., column 4.5×90 cm). The sample was dissolved in 60 ml of water and applied on the column which had been equilibrated with a mixture of acetonitrile-0.15% $KH_2PO_4$ (pH 3.5)=17:83 (v/v). The column was washed sequentially with 5 l each of acetonitrile-0.15% $KH_2PO_4$ mixture of the following ratios: 17:83, 18 82, 19:81, 20:80, and then developed with the same solvent mixture of a 22:78 ratio. The eluate was collected in 100 ml fractions which were monitored by the microplate assay using *C. albicans* A9540 and thin-layer chromatography ($SiO_2$, methyl acetate-n-propanol-28% ammonium hydroxide=45:105:60 v/v). The fractions containing the main homogeneous compound were combined and concentrated in vacuo to evaporate the organic solvent. The aqueous solution was loaded on a column of Diaion HP-20 (Mitsubishi Kasei, 8.0×25 cm), washed with 5 l of water, and then developed with 60% acidic aqueous acetone (pH 3.0) to elute the activity. Concentration of the active eluate followed by lyophilizaiton yielded 1.64 g of red homogeneous solid of BU-3608 HCl (purity:97%).

A solution of 1.6 g of BU-3608 HCl in 50 ml of 0.1N NaOH was diluted with 100 ml of n-propanol and 25 ml of methyl acetate. The mixture was kept in a refrigerator (5° C.) for three days to deposit fine needles of BU-3608 monosodium salt (1.43 g, purity: 99%). 100 mg of the sodium salt was dissolved in 20 ml of water and the solution adjusted to pH 5.0 with 1N HCl. The precipitate was filtered off and washed with cold water to give 91 mg of BU-3608 free form.

EXAMPLE 3

Isolation and purification of BU-3608 B and BU-3608 C

In the reversed phase silica gel chromatography procedure described in Example 2, the fractions eluting before and after the main homogeneous BU-3608 fraction were pooled. The combined eluate was desalted using HP-20 resin to afford a BU-3608 B-containing solid and a BU-3608 C-containing solid.

The BU-3608 B-containing solid (2.86 g) was dissolved in 200 ml of water and applied on a column of ODS-60 (Yamamura Chem. Lab. 8.0×90 cm) which had been thoroughly washed with a 22:78 (v/v) mixture of acetonitrile-0.15% $KH_2PO_4$ (pH 3.5). This same solvent mixture was used to elute the loaded column and fractions were collected and examined by HPLC. Fractions containing BU-3608 B were pooled, concentrated in vacuo. and desalted by HP-20 resin chromatography to yield impure BU-3608 (373 mg), pure BU-3608 (1.34 g) and BU-3608 B (66 mg). BU-3608 B was further purified by preparative HPLC using a Microsorb Short One $C_{18}$ column (4.6 mm I.D.×100 mm, 3 μm, Rainin Instrument Co.), and elution was carried out using 29:71 (v/v) mixture of acetonitrile-0.15% $KH_2PO_4$ (pH 3.5).

The BU-3608 C-containing solid (990 mg) was purified in a similar fashion using the ODS column with elution by a 21:79 (v/v) mixture of acetonitrile-0.15% $KH_2PO_4$ (pH 3.5). HPLC was used to monitor the eluate and fractions containing BU-3608 C were pooled and concentrated in vacuo. The resultant aqueous solution was desalted by HP-20 chromatography to yield nearly pure BU-3608 C (123 mg), and nearly pure BU-3608 (618 mg).

EXAMPLE 4

Preparation of BU-3608 B from BU-3608

BU-3608 hydrochloride (944 mg) was refluxed in 60 ml of 1.5N methanolic HCl for 4 hours. The reaction mixture was cooled and diluted with 200 ml of water. The solution was extracted with n-BuOH three times (100 ml each), and the extracts were combined and evaporated in vacuo to give the crude methyl ester of BU-3608 B (864 mg). The crude methyl ester (430 mg) was subjected to reversed phase silica gel chromatography (LiChoprep RP-18, 40-63μ, E. Merck column 4.0 cm I.D.×45 cm). The column was developed with a mixture of acetonitrile and 0.15% $KH_2PO_4$ adjusted to pH 3.5 by the addition of $H_3PO_4$ (40:60, v/v). Fractionation of the eluate was monitored by HPLC [Column: Microsorb Short One $C_{18}$, 4 6 mm I.D.×100 mm, 3 μm, Rainin Instrument Detection: UV 254 nm), Rt, methyl ester of BU-3608 B: 4.45 min., BU-3608: 2.03 min.]. Fractions containing the methyl ester of BU-3608 B were pooled and concentrated in vacuo to remove acetonitrile. The concentrate was charged on a column of Diaion HP-20 (200 ml) to desalt. The column was washed with water (500 ml) and eluted with 80% aqueous acetone adjusted to pH 3 by 1N HCl. Evaporation of the eluate yielded BU-3608 B methyl ester hydrochloride (144 mg). This chromatographic Procedure may be repeated for further purification.

The hydrochloride of BU-3608 B methyl ester (230 mg) was dissolved in 30 ml of 0.1 N NaOH, and the solution was refluxed for one hour. The resulting solution was acidified to pH 3.0 with 1N HCl, and desalted by HP-20 resin chromatography to yield BU-3608 B hydrochloride (220 mg).

EXAMPLE 5

Fermentation of BU-3608 C using actinomycete strain No. QZ78-4

Strain Q278-4 was grown on a slant of modified Bennett's agar medium which consisted of 0.5% glucose
0.1% fish extract (Mikuni)
0.1% yeast extract (Oriental Yeast)
0.5% NZ case (Sheffield)
0.2% NaCl
0.1% $CaCO_3$
1.6% agar The slant culture was incubated at 28° C. for 7 days.

A loopful of the slant culture was inoculated in a seed medium having the same composition as the slant culture except that agar was omitted. The seed culture was incubated at 28° C. for 4 days on a rotary shaker 200 rpm), after which time, 5 ml of the seed culture was transferred to a 500 ml Erlenmeyer flask containing 100 ml of a fermentation medium consisted of 2% soluble starch
1% Pharmamedia
0.5% $CaCO_3$
0.15% $(NH_4)_2SO_4$ The fermentation was carried out on a rotatory shaker 200 rpm) at 28° C. for 7 days. Antibiotic production in the fermentation broth was monitored by the broth dilution method using *Candida albicans* A9540 in Sabouraud dextrose broth. UV an HPLC assays were also employed. Antibiotic production reached a maximum on day 6 with approximately 160 μg/ml of BU-3608 C and approximately 240 μg/ml of BU-3608.

When the production medium was changed from 2% starch, 1% Pharmamedia, 0.5% $CaCO_3$, and 0.15% $(NH_4)_2SO_4$ to the production medium for strain P157-2 (Example 1, 3% glucose, 3% soybean meal, 0.5% Pharmamedia, 0.1 yeast extract, and 0.3% $CaCO_3$), the major product of the fermentation was BU-3608 with only a small amount of BU-3608 C produced.

EXAMPLE 5

Isolation and purification of BU-3608 C from Q278-4 fermentation 10.5 L of the harvested fermentation broth was centrifuged to remove the mycelial cake. The supernatant 10.0 l, pH 8.3) was acidified to pH 2.0 with the addition of 6N HCl and the resultant precipitate was filtered off. The filtrate was adjusted to pH 5.0 using 6N NaOH, and kept cool for two hours. The dark red precipitate was collected by filtration and then dissolved in 3 l of n-butanolmethanol-1% aqueous NaCl solution (3:1:4, pH 2.0). After the mixture was stirred for 30 minutes at room temperature, the organic layer was separated and extracted with two 500 ml portions of alkaline water (pH 8.0). The combined aqueous layer (1.5 l) was concentrated to 700 ml in vacuo. adjusted to pH 2.0, and applied to a column of Diaion HP-20 (300 ml). After the column was washed with 1.5 l of water, the active products were eluted with 60% aqueous acetone (pH 3.0). The red, active eluate was concentrated to afford an amorphous solid (900 mg) which, as determined by HPLC, contained BU-3608 C as a main component along with BU-3608 and other minor components.

The complex solid (880 mg) was applied to a reversed phase silica gel column (5.0 l YMC GEL ODS 60, Yamamura Chem. Lab.) which had been equilibrated with a 21:79 (v/v) mixture of acetonitrile-0.15% $KH_2PO_4$ (pH 3.5). The same solvent system was used to elute the column and the eluate was collected in 1 l fractions. Active fractions were assayed by HPLC (Microsorb Short One $C_{18}$ column, 4.6 mm I.D.×100 mm, 3 μm, Rainin Instrument Co.; 29:71 (v/v) mixture of acetonitrile-0.15% $KH_2PO_4$ (pH 3.5) as mobile phase at a flow rate of 1.2 ml/min.; UV absorption at 245 nm as detection). Fractions containing BU-3608 C were pooled and concentrated in vacuo. The aqueous concentrate was loaded on a column of HP-20 resin washed with water and eluted with aqueous acetone (pH 3.0). Evaporation of solvent from the eluate yielded BU-3608 C as red amorphous solid (227 mg, purity ≧98%).

EXAMPLE 6

Preparation of BU-3608 esters

Procedure 1

To a stirred solution of BU-3608 hydrochloride (290 mg) in 50 ml of ethanol was added dropwise 3 ml of thionyl chloride at 0° C. The stirring was continued for one hour at 0° C. and then for an additional two hours at room temperature. The reaction mixture was concentrated to dryness in vacuo and the residue was chromatographed on a reversed phase silica gel column (ODS-60, Yamamura Chemical Lab. 2.0×32 cm). Elution was carried out using a step gradient starting with acetonitrile-0.15% $KH_2PO_4$ buffer pH 3.5 (2:8) and ending with the ratio of 5:5. The fractions containing the desired product were pooled, concentrated in vacuo and desalted using a Diaion HP-20 column. The column was washed with water and then eluted with 80% aqueous acetone (pH 3.0 by 6N HCl). Concentration of the red eluate yielded 263 mg of BU-3608 ethyl ester hydrochloride. M.p. 218°–221 ° C. (dec.).

BU-3608 hydrochloride (150 mg) was similarly reacted in 25 ml of methanol and the reaction product was purified as described above to yield BU-3608 methyl ester hydrochloride (137 mg). M.p. 236°–239 ° C (dec.).

Similarly, BU-3608 cyclohexyl ester hydrochloride (54 mg) was obtained from BU-3608 hydrochloride (280 mg), cyclohexanol (13 ml) and thionyl chloride (2.5 ml). M.p. 206°–208° C. (dec.).

Procedure 2

To a solution of BU-3608 hydrochloride 82 mg) in dimethyl sulfoxide 1 ml) was added 2 ml of n-octanol followed by 1 ml of thionyl chloride at 0° C. The reaction mixture was worked up as described in Procedure 1 to give BU-3608 n-octyl ester hydrochloride (74 mg) after purification. M.p. 189°–192 ° C. (dec.).

n-Butyl ester of BU-3608 (488 mg) was similarly prepared from BU-3608 hydrochloride 550 mg), 5 ml of dimethyl sulfoxide and 15 ml of n-butanol. M.p. 208°–210° C. (dec.).

EXAMPLE 7

Preparation of AG-2 from BU-3608

BU-3608 (6.3 g) in 275 ml of 6N hydrochloric acid was heated at 115° C. for 14 hours in a sealed container. The mixture was cooled to room temperature. The precipitate was collected by filtration and then dissolved in alkaline water (pH 11). The solution was adjusted to pH 6.0, and the resultant precipitate was filtered off and charged on a column of Diaion HP-20 (2.6 l). The column was washed with water and eluted with 60% acetone. Lyophilization of the red eluate yielded 3.7 g of semi-pure AG-2. The sample was purified by Sephadex LH-20 chromatography (3.6 l) using 50% methanol as eluant to afford homogeneous AG-2 (3.2 g) as a red powder, m.p. 221°–223° C. (dec.).

MS (negative FAB): m/z 550 $(M+H)^-$.

$^1H$ NMR (400 MHz, DMSO-$d_6$) δppm: 1.33 (3H,d,J=7.3), 2.29 (3H,s), 3.90 (3H,s), 4.29 (1H),qui,J=7.3), 4.18 (2H, br-s), 5.56 (1H,br-s)*, 5.74 (1H,br-s)*, 6.71 (1H,d,J=2.2), 6.85 (1H,s), 7.11 (1H,d,J=2.2), 7.78 (1H,s), 8.41 (1H,d,J=7.2)*, 13.23 (1H,s)*, 14.87 (1H,br-s)*, * disappeared upon addition of $D_2O$.

$^{13}C$ NMR (100 MHz, DMSO-$d_6$) δppm: 17.4, 19.8, 47.9, 55.7, 71.6, 72.5, 103.9, 105.7, 110.2, 110.7, 114.9, 118.5, 118.6, 125.9, 131.8, 133.3, 136.2, 137.9, 140.5, 145.3, 157.1, 163.8, 165.5, 166.8, 168.1, 174.2, 180.2, 187.2.

Preparation of AG-2 methyl ester

AG-2(431 mg) was refluxed for 16 hours in 1.5N methanolic hydrogen chloride. The solution was evaporated in vacuo to dryness which was washed twice with 100 ml each of cold methanol. The insoluble AG-2 methyl ester was collected by filtration and dried in vacuo. Yield 402 mg. M.P. 210°–215° C. (dec.). MS(negative FAB): m/z 564$(M+H)^-$.

EXAMPLE 8

Preparation of BU-3608 from AG-2 methyl ester (1) To a stirred mixture of AG-2 methyl easter (5.63 g, 10 mmol), tetrabutylammonium hydrogensulfate (12 mg) and powdered NaOH (1 g) in dioxane (100 ml) is added dropwise a solution of acetyl chloride (2.83 g, 36 mmol) in dioxane (10 ml) over 30 min at room temperature. The mixture is filtered, washed with dioxane, evaporated and dried to give a residue. Chromatography of the residue on a column of silica gel using chloroform-methanol (4:1) as an eluant yields, 1,9,14-tri-O-acetyl AG-2 methyl ester.

(2) To a solution of 2-O-acetyl-3-O-(2,3,4-tri-O-acetylxylopyranosyl)-4-(N-tert-butoxycarbonyl)methylamino-4,6-dideoxygalactose (347 mg, 0.6 mmol) and pyridine (48 mg, 0.6 mmol in dry toluene (7 ml) is added thionyl chloride (91 mg, 0.6 mmol) at 5° C. The reaction mixture is kept at room temperature for 2 hrs and then filtered. The filtrate is washed with 0.2M phosphate buffer (pH 7) and then brine. dried over $MgSO_4$, concentrated and dried to afford a glassy solid. The solid is dissolved in dry methylene chloride (1 ml) and the solution was added to a stirred mixture of 1,9,14-tri-O-acetyl-AG-2 methyl ester (66.6 mg, 0.1 mmol), silver carbonate (200 mg), silver perchlorate (20 mg) and molecular sieves 3A (200 mg) in methylene chloride (3 ml). The reaction mixture is refluxed for 48 hrs in the dark under dry nitrogen atmosphere, filtered through a column of silica gel (3×3 cm) and washed throughly with a mixture of chloroform-methanol (4:1). The filtrate and washings are combined and solvent is evaporated to give an oil, which is acetylated with acetic anhydride (1 ml) in pyridine (7 ml) at room temperature for 18 hrs. The reaction mixture is poured on crushed ice and extracted with chloroform. The extracts are washed thoroughly with 0.4M $KHSO_4$ and brine, dried over $MgSO_4$, concentrated and dried to afford a solid. Column chromatography of the solid on silica gel using chloroform-ethanol (10:1) as an eluant yields octa-O-acetyl-N-tert-butoxycarbonyl BU-3608.

(3) To a solution of octa-O-acetyl-N-tert-butoxycarbonyl BU-3608 (55 mg, 0.05 mmol) in dioxane (3 ml) is added 0.1M Ba(OH)2 (3 ml) dropwise at 50° C. over 1 hr. The reaction mixture is neutralized with 0.1M H₂SO₄ (pH 7), filtered and washed with dioxane. The filtrate and washings are combined and evaporated to dryness. The resulting powder is dissolved in trifluoroacetic acid (2 ml) and kept at room temperature for 1 hr. The solvent is evaporated and the residue is purified by column chromatography on octadeoyl silicate (ODS, 10 ml) using as eluant a mixture of 0.15M phosphate buffer lpH 3.5 and CH₃CN (178:22) followed by HP-20 (5 ml) using 80% acetone as eluant to afford BU-3608.

If the procedure described in Steps (2)–(3) above is followed using the aminosugars listed below in place of 2-O-acetyl-30-(2,3,4-tri-O-acetylxylopyranosyl)-4-(N-tert-butoxycarbonyl)methylamino-4,6-dideoxygalactose, the corresponding glycosides are obtained.

2-O-acetyl-3-O-(2,3,4-tri-O-acetylxylopyranosyl)-4-(N-tert-butoxycarbonyl)amino-4,6-dideoxygalactose
2,3-di-O-acetyl-4-(N-tert-butoxycarbonyl)amino-4-deoxyglucose
2,3-di-O-acetyl-4-(N-tert-butoxycarbonyl)methylamino-4,6-dideoxygalactose
2,3-di-O-acetyl-4-(N-tert-butoxycarbonyl)methylamino-4,6-dideoxyglucose

What is claimed is:

1. An antibiotic having the formula

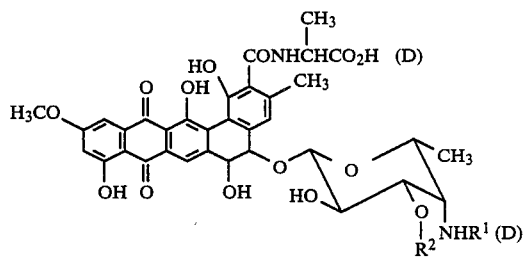

wherein $R^1$ is H and $R^2$ is β-D-xylosyl; or $R^1$ is methyl and $R^2$ is β-D-xylosyl; or a base salt, acid addition salt or internal salt thereof, or ester of the carboxylic acid group.

2. The compound of claim 2 wherein said salt is the sodium salt.

3. The compound of claim 2 wherein said salt is the hydrochloride salt.

4. The compound of claim 1 which is

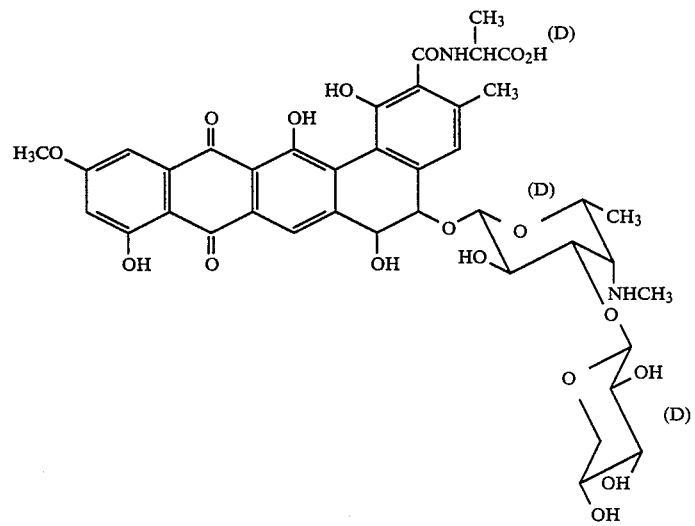

5. The compound of claim 4 wherein said ester is selected from the group consisting of methyl, ethyl, n-butyl, cyclohexyl, and n-octyl.

6. The compound of claim 1, which is

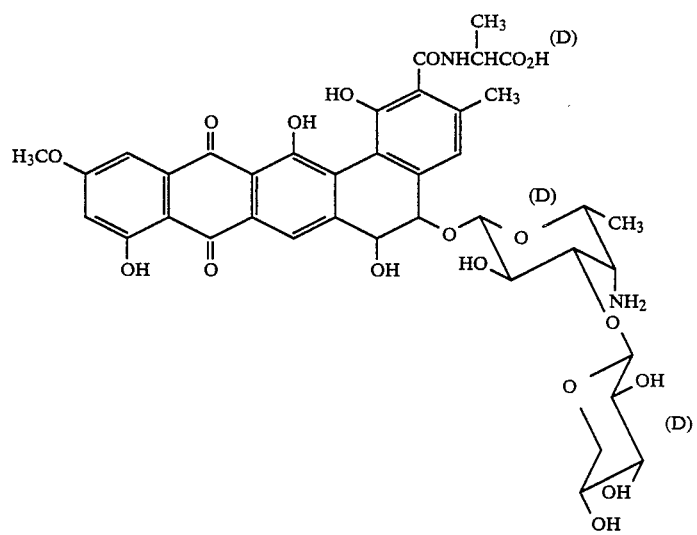

UNITED STATES PATENT AND TRADEMARK OFFICE
CERTIFICATE OF CORRECTION

PATENT NO. : 4,870,165
DATED : September 26, 1989
INVENTOR(S) : Toshikazu Oki, et al.

It is certified that error appears in the above-identified patent and that said Letters Patent is hereby corrected as shown below:

In the specification:

Column 13, Line 25: The portion beginning with the word "phospholipid" and running to the end of Line 53 of the same column should be moved to Column 12, Line 34, after the word "PIV", and the period after "PIV" should be deleted.

In the claims:

Claim 2, Line 19: Delete "2" and substitute -- 1 --.

Claim 3, Line 21: Delete "2" and substitute -- 1 --.

Signed and Sealed this

Seventeenth Day of March, 1992

Attest:

HARRY F. MANBECK, JR.

*Attesting Officer*     *Commissioner of Patents and Trademarks*